(12) United States Patent
Coilard-Lavirotte et al.

(10) Patent No.: US 8,262,712 B2
(45) Date of Patent: Sep. 11, 2012

(54) PHALANGEAL ARTHRODESIS IMPLANT, SURGICAL KIT AND METHOD FOR MANUFACTURING SAME

(75) Inventors: Jean-Yves Paul Albert Coilard-Lavirotte, Saint Cyr Aux Monts D'Or (FR); Olivier Laffenetre, Bordeaux (FR)

(73) Assignee: New Deal, Lyons (FR)

( * ) Notice: Subject to any disclaimer, the term of this patent is extended or adjusted under 35 U.S.C. 154(b) by 1244 days.

(21) Appl. No.: 11/940,628

(22) Filed: Nov. 15, 2007

(65) Prior Publication Data

US 2008/0132894 A1 Jun. 5, 2008

(30) Foreign Application Priority Data

Nov. 16, 2006 (FR) .................................. 06 10043

(51) Int. Cl.
*A61B 17/04* (2006.01)
*A61B 17/84* (2006.01)
*A61F 2/08* (2006.01)
(52) U.S. Cl. .................. 606/300; 606/78; 623/21.15
(58) Field of Classification Search .................. 606/326, 606/327, 329, 330, 78; 623/21.11, 21.15, 623/21.19
See application file for complete search history.

(56) References Cited

U.S. PATENT DOCUMENTS

| 5,713,904 A | 2/1998 | Errico et al. |
| 2005/0283159 A1 | 12/2005 | Amara |
| 2006/0084998 A1* | 4/2006 | Levy et al. ..................... 606/63 |

FOREIGN PATENT DOCUMENTS

| FR | 2653006 | 4/1991 |
| FR | 2778082 | 11/1999 |
| FR | 2787313 | 6/2000 |
| WO | 03007830 A1 | 1/2003 |
| WO | 2005096975 A2 | 10/2005 |

OTHER PUBLICATIONS

Search Report for French Patent Application No. 0610043; Jun. 29, 2007.

* cited by examiner

*Primary Examiner* — Andrew Yang
(74) *Attorney, Agent, or Firm* — Jason A. Bernstein; Barnes & Thornburg LLP

(57) ABSTRACT

A medical implant interposable between a first bone and a second bone in order to support the first and second bones substantially joined one to the other, so as to obtain bony fusion of the first and second bones. Also disclosed is a surgical kit comprising an implant and a surgical instrument for bony preparation. Also disclosed is a method for manufacturing a medical implant.

24 Claims, 2 Drawing Sheets

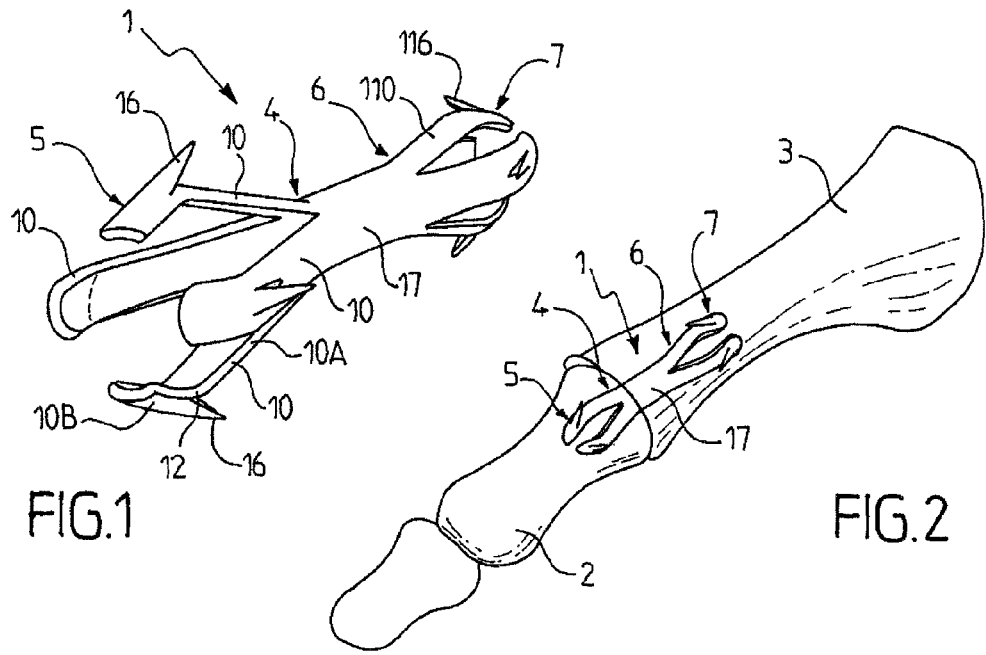
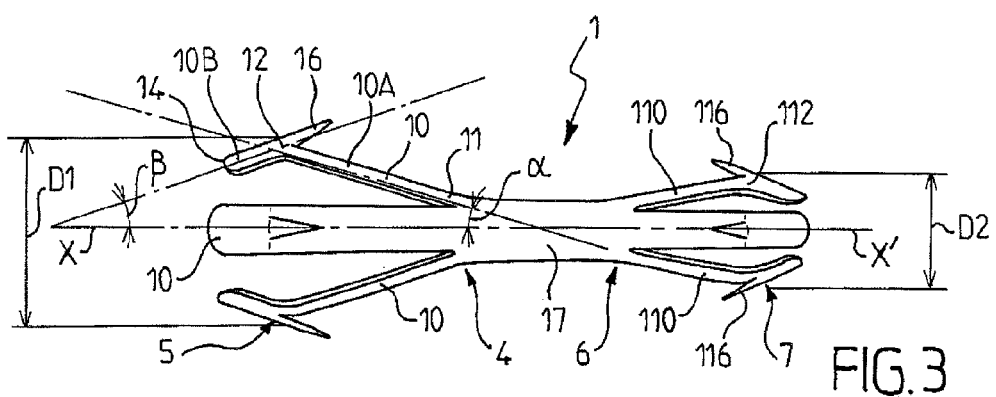
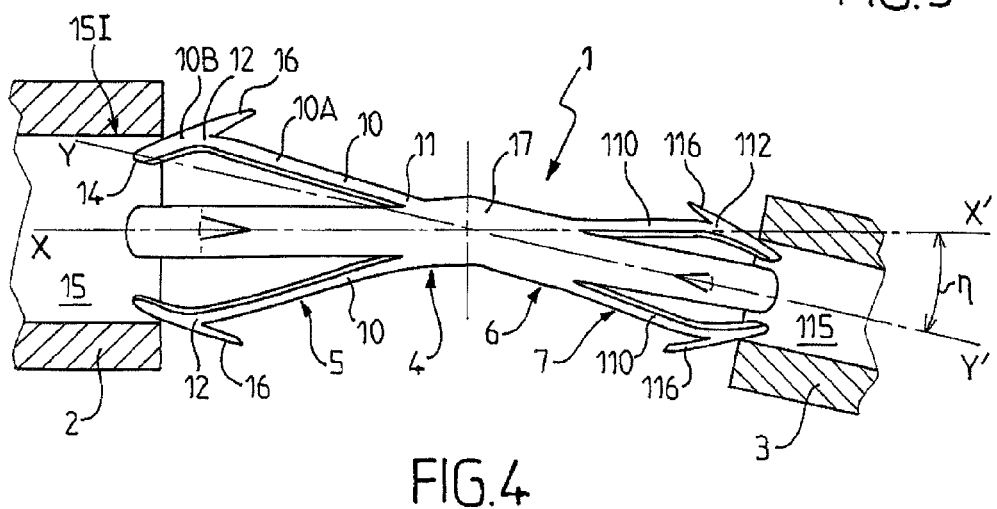

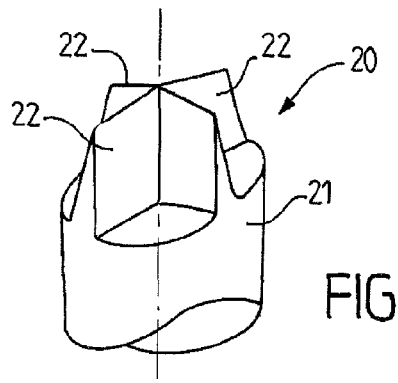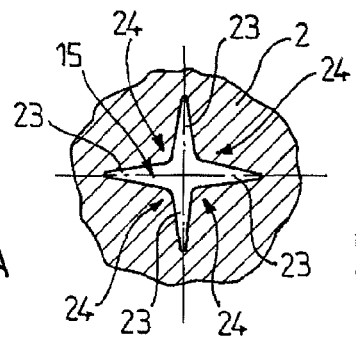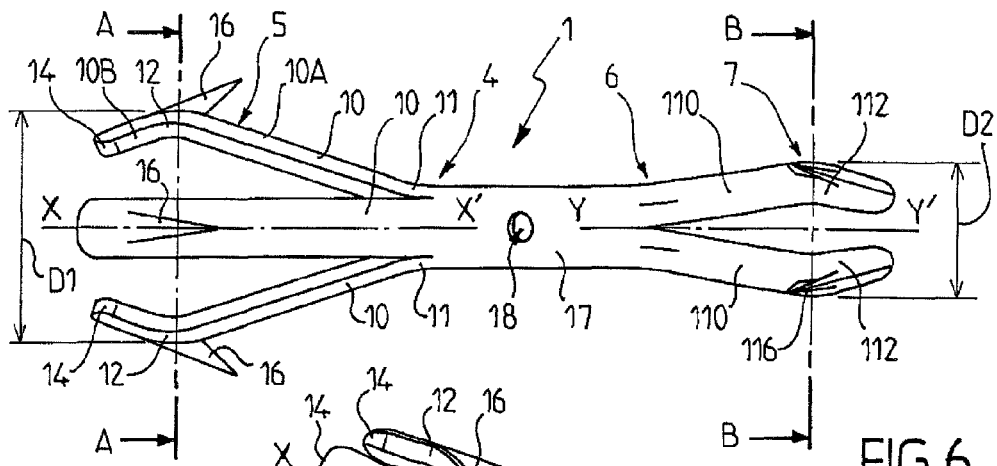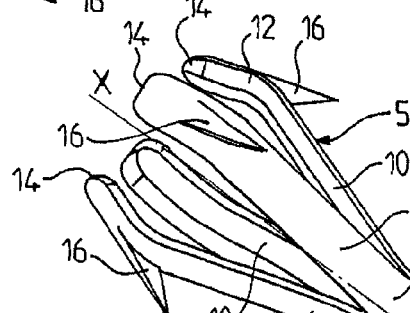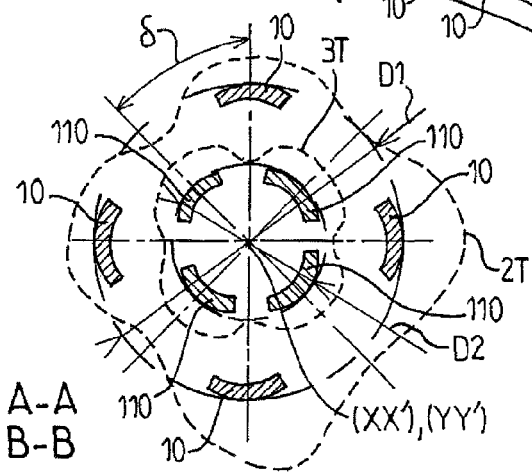

PHALANGEAL ARTHRODESIS IMPLANT, SURGICAL KIT AND METHOD FOR MANUFACTURING SAME

PRIORITY CLAIM

This patent application claims priority to French Patent Application No. 0610043, filed Nov. 16, 2006, the disclosure of which is incorporated herein by reference in its entirety.

FIELD

The present disclosure relates to medical implants intended to be fixed in bones during operations related to orthopaedic surgery, in particular, to implants used to assemble bones or bone fragments in order to join them by bone fusion.

The present disclosure relates more particularly to a medical implant intended to be interposed between a first bone and a second bone in order to support the bones joined substantially to one another so as to obtain bone fusion of the bones.

The present disclosure also relates to a surgical kit.

Finally, the present disclosure relates to a method for manufacturing a medical implant provided with a means of fixing arranged to hold the implant in a bone.

BACKGROUND

In the orthopaedic surgery field, several operations are intended to fix one tissue to another in order, for example, to facilitate the taking of a graft, to restore a natural link between tissues after the link has been damaged or destroyed by an illness or by trauma, to consolidate a bone or even to strengthen a broken joint.

In particular, the practice of fitting an arthrodesis, i.e., forced immobilisation of the joint in question by triggering a bony fusion between the bones which constitute the joint, is known with patients suffering from major articular lesions, in particular, severe arthritis which has led to damage to the cartilaginous and/or bony articular surfaces.

The arthrodesis can, for example, be fitted to inter-phalangeal joints, in particular, the foot, and employ different surgical techniques.

One exemplary surgical technique consists of resecting the ends of two consecutive phalanges which have to be fused in order to create surfaces termed "bleeding," to place the bleeding surfaces obtained in contact with one another, and then to fit a fixing implant intended to facilitate regeneration of the bony tissues at the contact interface.

To this end, the introduction of a pin, i.e., a fine cylindrical metal rod in line with the medullary axis of the phalanges, wherein the pin crosses the joint from side to side and limits the radial movement of one phalange relative to the other, is known.

One variant of this technique consists of using a screw rather than a pin, the screw is from the end of the finger in line with the medullary axis of the distal phalange so as to cross the joint and support the two phalanges compressed against one another.

Although these arthrodesis implants generally are satisfactory in therapeutic terms, the arthrodesis implants, however, suffer from drawbacks that are not negligible related, in particular, to the quality of the mechanical link produced between the tissues, and, more particularly, between the bones which the arthrodesis implants are supposed to support.

Indeed, the above-mentioned implants provide only partial mechanical support for the first bone against the second, more particularly, for the first phalange relative to the second, which tends to retard and complicate the reconstitution of a bony tissue at the contact interface of the bones.

More precisely, if the patient moves the member in question, for example, when walking if this is an arthrodesis implanted in the foot, the mechanical stresses applied to the joint can be the source of unwanted relative movements of the bones which are liable to lead to tearing and abrasion of the tissue being formed.

For example, the bones are liable to slide along the pin and thus separate axially from one another or even to rotate about the axis formed by the pin. Similarly, a medullary screw may slacken under the effect of relative rotation of the first bone in relation to the second, while allowing relative movement of the bones.

Moreover, arthrodesis implants from the prior art generally expose the patient to trauma of the tissues of the joint located in the vicinity of the treated joint. Thus, a medullary pin is liable to move longitudinally until the pin is just supported against the cortical tissues or the soft tissues located in the lengthening of the axis of extension or even to perforate the tissues. The projection formed by the head of the screw comes into contact with the surrounding tissues of the joint and thus form a painful point of compression and causes premature wear of the tissues.

Next, the forced position in which the arthrodesis implants from the prior art block the joint frequently differs from the natural anatomy of the patient, which generates a situation of discomfort or even pain for the patient.

Finally, arthrodesis implants from the prior art generally need significant surgical preparation of the joint and are of significant bulk which tends to make the operation long, complex and traumatic for the patient.

SUMMARY

The present disclosure describes several exemplary embodiments of the present invention.

One aspect of the present disclosure provides a medical implant interposable between a first bone and a second bone in order to support the first and second bones substantially joined one to the other, so as to obtain bony fusion of the first and second bones, the implant, comprising at least one first section designed to be introduced into the first bone having a first means of fixing arranged to hold the implant in the first bone, as well as a second section designed to be introduced into the second bone and having a second means of fixing arranged to hold the implant in the second bone, wherein the first means of fixing incorporates a plurality of non-coplanar anchoring branches integral with the first section which are intended to create a built-in link between the implant and the first bone, wherein anchoring branches are splayed during manufacture of the implant so that, before installation of the implant in the bones, a divergent portion opens outward relative to the first section and the ends of a convergent portion substantially turn down in order to facilitate the introduction of the implant into the first bone.

Another aspect of the present disclosure provides a surgical kit, comprising a) an implant interposable between a first bone and a second bone in order to support the first and second bones substantially joined one to the other, so as to obtain bony fusion of the first and second bones, the implant comprising at least one first section designed to be introduced into the first bone having a first means of fixing arranged to hold the implant in the first bone, as well as a second section designed to be introduced into the second bone and having a second means of fixing arranged to hold the implant in the second bone, wherein the first means of fixing incorporates a plurality of non-coplanar anchoring branches integral with the first section which are intended to create a built-in link between the implant and the first bone, wherein anchoring branches are splayed during manufacture of the implant so that, before installation of the implant in the bones, a divergent portion opens outward relative to the first section and the ends of a convergent portion substantially turn down in order to facilitate the introduction of the implant into the first bone; and b) a surgical instrument for bony preparation, the instrument comprising a punch having a plurality of prominent elements arranged so as to mark simultaneously in the bone, by percussion, an imprint comprising a plurality of cavities intended to accommodate the anchoring branches of the implant, the arrangement of the cavities are substantially conjugate to that of the anchoring branches.

A further aspect of the present disclosure provides a method for manufacturing a medical implant, comprising a) producing the first means of fixing during which an oblong part is cut so as to divide a fraction of the oblong part into a plurality of the non-coplanar anchoring branches integral with the oblong part, further comprising a sub-step (a2) for deploying the divergent portion during which the anchoring branches are folded outward so as to cause them to diverge according to a substantially tapered distribution, as well as a sub-step (a3) forming a convergent portion during which the free ends of the anchoring branches are turned down by folding toward the axis of extension of the oblong part.

The features of the present disclosure remedy the above-mentioned drawbacks and propose a new medical implant which could be fixed solidly and stably in a bone.

Another feature of the present disclosure proposes a new medical implant intended to be fixed in a bone which is particularly easy to use.

Another feature of the present disclosure proposes a new medical implant of simple and compact form having little bulk.

Another feature of the present disclosure proposes a new medical implant which is particularly inexpensive to manufacture.

Another feature of the present disclosure proposes a new medical implant which will be particularly atraumatic and which is comfortable to use for the patient.

The features of the present disclosure propose a new surgical kit which is extremely easy to use and allows a rapid, simple and sure implementation of the implant of the present disclosure.

Another further feature of the present disclosure proposes a new method of manufacturing a medical implant capable of providing the implant with a means of fixing in the bone which is sure and effective.

Finally, another feature of the present disclosure proposes a new method of manufacturing a medical implant which is particularly simple and economic to use.

The present disclosure describes a medical implant intended to be interposed between a first bone and a second bone substantially joined one to the other in order to obtain the bony fusion of the bones, the implant having at least one first section designed to be introduced into the first bone and provided with a first means of fixing arranged to hold the implant in the first bone, as well as a second section designed to be introduced into the second bone and provided with a second means of fixing arranged to hold the implant in the second bone, the first means of fixing incorporating a plurality of non-coplanar anchoring branches integral with the first section which are intended to create a built-in link between the implant and the first bone, the implant wherein the anchoring branches are splayed in manufacture in order to present, before fitting the implant in the bones, a divergent portion which opens outwards in relation to the first section as well as a convergent portion turning down its ends substantially in order to facilitate introduction of the implant into the first bone.

The present disclosure describes a surgical kit comprising:
first a medical implant as in the present disclosure,
and second a surgical instrument intended for bone preparation, the instrument comprising a punch which has a plurality of prominent elements arranged to mark simultaneously in the bone, by percussion, an imprint comprising a plurality of cavities intended to house the anchoring branches of the implant, the arrangement of the cavities being substantially conjugate to that of the anchoring branches.

The present disclosure describes a method of manufacturing a medical implant of the present disclosure, the method comprising a step (a) for producing the first means fixing during which an oblong part is scored so as to divide a fraction of the oblong part into a plurality of non-coplanar anchoring branches integral with the oblong part, comprising the step (a) for producing the first means of fixing includes a sub-step (a2) for deploying the divergent portion, during which the anchoring branches are folded towards the outside so as to make them diverge according to an substantially sectional distribution, as well as a sub-step (a3) for forming the convergent portion during which the anchoring branches are divided by folding the free ends towards the axis of extension of the oblong part.

BRIEF DESCRIPTION OF THE DRAWINGS

Various aspects of the present disclosure are described hereinbelow with reference to the accompanying figures.

FIG. 1 is an isometric view of one exemplary embodiment of an implant according to the present disclosure;

FIG. 2 is an isometric view of one exemplary embodiment of an implant according to the present disclosure used for an inter-phalangeal arthrodesis;

FIG. 3 is a side elevation of the implant of FIG. 1;

FIG. 4 is a side elevation of another exemplary embodiment of an implant according to the present disclosure showing the introduction of the implant into the bone in diagram form;

FIG. 5A is an isometric view of a portion of a surgical instrument intended for a surgical kit according to the present disclosure;

FIG. 5B is a cross-section of an imprint which can be marked in a bone using the instrument of FIG. 5A;

FIG. 6 is a plan view of an exemplary embodiment of an implant according to the present disclosure;

FIG. 7 is an isometric view of the implant of FIG. 6; and

FIG. 8 is a single side elevation of the cross-sections Λ-Λ and B-B of the implant of FIG. 6, shown in a single drawing.

DETAILED DESCRIPTION

The medical implant of the present disclosure, hereafter "implant", is intended to be introduced into the body of a human or animal patient in order to achieve the fixing of one tissue with another tissue.

More precisely, the implant 1 is intended to be interposed between a first bone 2 and a second bone 3 in order to support the first and second bones 2, 3 joined substantially to one another in order to obtain bony fusion of the bones.

The implant 1 is more preferably an arthrodesis implant, although use in other applications could be considered, such as the reduction and consolidation of fractures.

Moreover, the implant 1 is more preferably an intramedullary implant, in particular, intended to be engaged in the diaphysis and/or apophysis of the first bone (the second respectively) according to a direction near to the medullary axis of the latter.

Within the meaning of the present disclosure, the first and/or the second bone may indifferently be naturally present in the treated zone or added in the form of grafts, endogens or exogens.

In a particularly preferred manner, the first bone 2 and the second bone 3 are phalanges, the implant 1 then forming an inter-phalangeal arthrodesis implant. More specifically, the implant is more preferably designed to be implanted in a patient's foot and support the mechanical stresses associated with walking.

The implant 1 has at least a first section 4 designed to be introduced into the first bone 2 and provided with a first means 5 of fixing arranged to hold the implant 1 in the first bone 2.

According to the present disclosure, the implant 1 also has a second section 6 designed to be introduced into the second bone 3 and provided with a second means 7 of fixing arranged to hold the implant 1 in the second bone 3.

According to one feature of the present disclosure, the first means 5 of fixing includes a plurality of anchoring branches 10 integral with the first section 4 and arranged according to a non-coplanar layout so as to create a built-in link between the implant 1 and the first bone 2.

For purposes of the present disclosure, the term "built-in link" is a kinematic link in which all degrees of freedom, i.e., the three degrees of freedom in translation and the three degrees of freedom in rotation, are suppressed. In other words, the first means 5 of fixing is designed to fix the implant 1 to the first bone 2 so that the first bone 2 forms only a single unit on the kinematic plane.

For purposes of the present disclosure, the term "non-coplanar layout" means that the anchoring branches 10 form a network which is extended according to the three dimensions of the space. Indeed, if the anchoring branches were extended substantially according to a single plane of the space, i.e., occupied a region of space inscribed in a rectangular parallelepiped in which the length and/or the width are clearly greater than the thickness, the fixing would risk a lack of stability, as play between the implant 1 and the bone 2 is liable to appear and/or as distortion by flexing of the first means 5 of fixing according to an axis contained in the plane is liable to occur (the first means 5 of fixing tending to "fold" under stress).

It is foreseeable that the non-coplanar layout of the anchoring branches 10 should be obtained by means of two anchoring branches which are curved so as to exhibit together at least three segments of length sufficient and divergent directions between them. However, this solution would risk complicating the fitting of the implant 1. This is why the first means 5 of fixing includes more preferably at least three, and most preferably four, anchoring branches 10.

Advantageously, the multiplication of the securing points thus created by the anchoring branches can improve the seating of the implant in the bone and, consequently, the stability of the fixing, each anchoring branch 10 playing in the network formed by the other anchoring branches 10 the role of a strut which contributes to the rigidity of the fixing.

For convenience in description, reference will be made in what follows to anchoring branches 10 in their entirety, although it may be considered that each anchoring branch 10 must be subject independently to production variations according to any combination of one or another of the characteristics detailed below.

According to the present disclosure, the anchoring branches 10 are "integral with the first section 4", i.e., they are fixed as a built-in link with the first section 4. For purposes of the present disclosure, there is neither play nor any movement possible, other than that by any intrinsic distortion of the materials under stress, of the anchoring branches 10 relative to the first section 4 to which the anchoring branches 10 are attached.

It can be remarked that this intimate link of the anchoring branches 10 with the first section 4 should exist more preferably before fitting the implant 1 and more precisely before introducing the first section 4 into the first bone 2. In other words, the anchoring branches 10 are more preferably designed to be used concomitantly with the introduction of the first section 4 into the first bone 2, and not added after the introduction operation.

According to one preferred exemplary embodiment, the anchoring branches 10 are made from the same material as the first section 4.

More preferably, the anchoring branches 10 are distributed as a corolla around the first section 4. Advantageously, this distribution, more preferably substantially uniform, can balance the range of support from the implant 1 against the bone 2 and improve the stability of the fixing.

Although it is conceivable that the first means 5 of fixing is positioned in any zone of the implant 1, the first section 4 is more preferably located at one end of the implant 1, and the anchoring branches 10 extend more preferably from the first section 4 and substantially beyond the end, as is illustrated in FIGS. 1-4.

In other words, the anchoring branches 10 are more preferably located in the end of the implant 1 and directed substantially towards the outside of the implant. In particular, if the first section 4 forms the distal end of the implant 1, the anchoring branches point more preferably from the first section 4 in a direction substantially opposed to the near end of the implant.

More preferably, the first section 4, and more generally the implant 1 in its entirety, is substantially oblong.

Although it is foreseeable that the anchoring branches are contained in a virtual envelope formed by extending the first section 4 beyond the end at which the first section is located, the anchoring branches 10 extend more preferably toward the end beyond the envelope in order to maximize the extent of the anchoring in the bone, i.e., the range of the first means 5 of fixing.

More precisely, as illustrated in FIGS. 1-4, the first section is extended more preferably according to a first axis of extension (XX'), the anchoring branches 10 include a divergent portion 10A which diverges from the axis of extension (XX') from the first section 4.

In other words, the spatial arrangement of the material constituting the anchoring branches 10 comprises at least one centrifugal radial extension component relative to the first axis of extension (XX'), such that the divergent portions 10A open outward relative to the first section 4.

The angle of opening α of the divergent portion relative to the first axis of extension (XX') is more preferably substantially between 5° and 20° inclusive.

Although the anchoring branches 10 could be formed by secant plates substantially joining (united, for example, according to a cruciform assembly), the branches are more preferably longilineal and disjointed, a basic portion 11 attaching them to the first section 4. Moreover, although the anchoring branches 10 could be divided, the anchoring branches 10 are more preferably substantially linear. This arrangement favours, in particular, the penetration of the branches into the bone.

Furthermore, the anchoring branches 10 could be staged along the first section 4, for example, as ears or as chevrons, or even emerge from a single common basic portion 11.

In a particularly preferred manner, the anchoring branches 10 are all substantially of the same shape, the same dimensions and distributed in an equidistant manner around the first section 4.

Thus, the divergent portions 10A of the anchoring branches are more preferably contained substantially within the space included between an internal sectional envelope of the axis (XX') and the angle at the apex equal to 10° and an external sectional envelope of the same axis (XX') and the angle at the apex equal to 40°.

According to one important feature of the present disclosure, the anchoring branches 10 are splayed during manufacture, as will be described in more detail hereafter.

In other words, the anchoring branches 10 are preformed at source during construction, before the introduction and fitting of the implant in the bone or bones 2, 3.

In particular, the divergent portions 10A are pre-oriented by construction in order to present their divergent character intrinsically and not to be adopted after installation.

In a particularly preferred manner, the implant 1 of the present disclosure is devoid of means of splaying, its own or added, liable to modify actively the geometric configuration during or after installation, and more precisely liable to deploy radially the anchoring branches 10 beyond the space which the anchoring branches 10 occupy before installation, for example, by forcing plastic distortion under stress of the anchoring branches 10.

The implant 1 may thus have a particularly simple and intrinsically stable structure in which the support is autonomous and substantially non-varying. The use of such an implant 1 limits advantageously any risk of a bone cracking or of relative uncontrolled movement of a bone 2, 3 relative to the other once the implant is introduced into the bone.

According to another important feature of the present disclosure, as is illustrated in FIGS. 1-4, the anchoring branches 10 also have a convergent portion 10B which turns down the ends substantially in order to facilitate introduction of the implant 1 into the first bone 2.

Thus, overall, the anchoring legs 10 have a discontinuity in the slope which confers on the anchoring legs 10, relative to the outside, according to a direction at right angles to the axis of extension (XX'), a profile that is convex overall (and, more particularly, in an oblate tubular V).

Within the meaning of the present disclosure, the convergent or divergent character of the portions of the anchoring branches 10A, 10B is more preferably continuous over the full length of the portion in question. However, it is possible that a single portion of the anchoring branch should be subject locally to variations of separation from the axis (XX'), such as undulations, while maintaining overall its divergent or convergent character.

More preferably, the anchoring branches 10 have at least one bend 12, i.e., a change of direction between two adjacent surfaces or two consecutive segments which form a prominent angle.

Advantageously, the bend 12 marks a transition that is substantially continuous between the divergent section 10A and the convergent section 10B and, more preferably, forms a portion that is rounded overall and of substantially constant thickness, which is substantially equal to those of the adjacent portions 10A, 10B.

Of course, it is perfectly foreseeable within the meaning of the present disclosure that the anchoring branches 10 have more than two distinct successive portions and, for example, comprise three portions forming respectively one "large" divergent portion, followed by two "small" convergent portions, one intermediate and the other terminal, placed in succession and each turning the branch down gradually towards the first axis of extension (XX').

However, the anchoring branches 10 will more preferably comprise only two successive portions, which form respectively a divergent portion 10A extending between one captive end of the first section 4 and the bend 12, then a convergent portion 10B which extends between the bend 12 and a free end opposite the first section 4, which can advantageously be totally separate from the other elements constituting the implant. This arrangement confers advantageously a certain structural and functional flexibility on the first means 5 of fixing, and favours a slight functional elastic distortion of the divergent portion 10A, at the time of introducing the implant, which ensures an excellent engagement in the bone.

Thus, more preferably, as is illustrated in FIGS. 1-4, the bend 12 marks the transition between the divergent portion 10A and a convergent portion 10B which extends from the bend 12 up to one free end 14 of the anchoring branch 10, the free end 14 being substantially turned down towards the first axis of extension (XX').

The bend 12 then forms the apex or "culminating point" of the anchoring branch 10, i.e., the part most remote from the axis of extension (XX').

According to one preferred exemplary embodiment, the angle of closure β according to which the convergent portion 10B is oriented relative to the first axis of extension (XX') is substantially between 0° and 30° inclusive.

Thus, by construction, the angle of the angular sector delineated by the bend 12 and included between the axis of extension (XX') and the bend 12 is more preferably substantially between 130° and 175° inclusive.

It should be noted that if β=0°, the angle of divergence between the divergent portion 10A and the convergent portion 10B is equal to the value of the angle of opening α, whereas the convergent portion 10B extends substantially parallel to the axis of extension (XX').

If β>0°, the convergent portion 10B tends to approach the terminal portion of anchoring branch 10 of the first axis of extension (XX').

Advantageously, by curving the anchoring branch 10 as in the present disclosure, an engagement ramp can be formed which facilitates the introduction of the anchoring branch 10, and more generally the implant 1, into the bone 2. More globally, the anchoring branches 10 and, more particularly, their convergent portions 10B can form in their whole a point that is substantially conical penetrating into the bone.

Moreover, as is illustrated in FIG. 4, such a ramp can advantageously cooperate with the internal wall 151 of a hollow housing 15 in the first bone 2 such that, if the convergent portion 10B slides along the wall, the latter exerts a stress which tends to flex the anchoring branch 10 by turning the anchoring branch 10 down toward the first axis of extension (XX'). In a particularly advantageous manner, the anchoring branches 10, under the effect of elastic distortion, and, more particularly, by deflecting their divergent portion 10A, can thus exert a pressure against the internal wall 151 of the housing 15, the housing 15 exerting in return, according to the action-reaction principle, a substantially concentric locking effect on the means 5 of fixing.

The anchoring branches 10 are thus more preferably splayed "like an umbrella" so as to form substantially the generators of a virtual bi-conical envelope in which the axis coincides substantially with the first axis of extension (XX') and in which the largest basic diameter D1 is the same as that of the virtual circle passing through the bends 12.

Furthermore, the length of the divergent portion 10A accounts more preferably for 50% to 90% of the total length of an anchoring branch 10, whereas the length of the convergent portion 10B accounts more preferably for 10% to 50% of the total length of the anchoring branch 10.

In other words, the "introduction turn-down" formed by the convergent portion 10B is substantially shorter than the "fixing pad" formed by the corresponding divergent portion 10A.

Moreover, the anchoring branches 10 will more preferably have, over the major part if not all of their length, substantially constant transverse dimensions, and, in particular, thickness (i.e., a substantially constant cross-section). This arrangement can, in particular, be obtained in a very simple manner as will be described in more detail hereafter by manufacturing the implant starting with a roughly tubular format.

Secondly, although the divergent portions 10A and the convergent portions 10B extend more preferably in a substantially rectilinear manner, it is also foreseeable that the divergent portions 10A and the convergent portions 10B are, one and/or the other, curved according to the longitudinal direction of extension and have a shape that is substantially curved in, concave or convex.

To improve the fixing of the implant 1 and, in particular, to block the implant 1 according to the first axis of extension (XX') after introduction into the first bone 2, and, more particularly, into the housing 15, the prominent apex of the bend 12 is more preferably provided with an anti-return device 16, such as a barb or a lug, arranged to permit movement of the first section 4 in the direction of penetration into the bone and to oppose extraction out of the first bone 2 of the corresponding anchoring branch 10. More precisely, the barb is intended to engage in the wall 151 of the housing 15 in order to anchor the branch 10 in the bony tissue. Advantageously, the penetration of the anti-return device 16 into the internal wall is facilitated by the piling stress from the bend 12 against the internal wall which the anchoring branch 10 exerts, and, more particularly, the divergent portion 10A of the anchoring branch 10, under the effect of elastic distortion.

Support in translation along the first axis of extension (XX') of the first section 4 according to the direction of introduction into the first bone 2 can, for example, be provided either by abutting the free ends 14 against the housing 15, if the housing 15 is one-eyed, either by imprisoning bony matter inside the space included between the anchoring branches 10 at the time of the introduction, the accumulated material forming a cushion opposing migration of the implant 1.

For purposes of the present disclosure, the second means 7 of fixing is not limited to a particular embodiment and may notably call upon various solutions of mechanical fixing, such as screws, pins, hooks or the like.

However, in a preferred manner, the second means 7 of fixing reproduces substantially the solutions employed by the first means 5 of fixing, the arrangement and the functions of the second means 7 of fixing being deduced from those of the first means 5 of fixing mutatis mutandis.

For convenience of description, the different elements constituting the second means 7 of fixing will be numbered by using the references, incremented by a value of 100, of the similar elements constituting the means 5 of fixing.

More particularly, the second means 7 of fixing includes more preferably a plurality of anchoring branches 110 integral with the second section 6 and arranged according to a non-coplanar layout in order to create a built-in link between the implant 1 and the second bone 3.

In addition, the anchoring branches 110 are splayed during manufacture in order to have a divergent portion which is open to the outside relative to the first section as well as a convergent portion turning down substantially at the ends in order to facilitate the introduction of the implant 1 into the second bone 3.

In a particularly preferred manner, the implant 1 is substantially oblong and the second section 6 is located at the end of the implant which is opposite the first section 4.

In a preferred manner, as illustrated in FIGS. 1-4, the anchoring branches 110 associated with the second section 6 are also distributed in a corolla around the second section 6 and extend beyond the corresponding end of the implant 1 in a direction substantially opposite to that of the anchoring branches 10 associated with the first section 4.

According to one exemplary embodiment which is not depicted, the conformation of the second means 7 of fixing is identical to that of the first means 5 of fixing.

In particular, the implant 1 can be produced by placing end to end two sections 4, 6 arranged top to bottom, the sections are holders of means 5, 7 of fixing, strictly identical with those of the present disclosure, so as to form an implant 1 having a mirror plane of symmetry substantially normal to the first axis of extension (XX').

However, it is perfectly foreseeable that the conformation of the second means 7 of fixing differs from that of the first means 5 of fixing by its geometry, by its dimensions, by the number of anchoring branches each associated with the respective sections, and by the number and orientation of the bends, etc.

Thus, as depicted in FIGS. 1, 3, 4, 6 and 7, the conformation of the second means 7 of fixing differs more preferably from that of the first means 5 of fixing by its dimensions, and more specifically by the length of its anchoring branches 110, and/or by the angle of opening of the latter relative to axis of extension of the second section 6.

In particular, if it is considered that the anchoring branches 10, 110 are splayed "like an umbrella" in order to form substantially the generators of a pair of virtual bi-conical envelopes in which the respective axes coincide substantially with that of the corresponding section and in which the largest basic diameter ("overall diameter") is the same as that of the virtual circle passing through the bends 12, 112, it is particularly advantageous that the overall diameter D1 at rest of the first means 5 of fixing located on the distal end of the implant should be greater than the largest overall diameter D2 at rest of the second means 7 of fixing located at the proximal end of the implant 1.

Indeed, if the ends of the phalanges are resected, the proximal phalange, i.e., closest to the ankle if this is a phalange in the foot, has a relatively narrow head, whereas the base of the corresponding distal phalange, that which is closest to the toes, is substantially broader. Thus, an asymmetrical implant can advantageously share to best effect the anchoring volume available in each phalange by maximizing the range of the corresponding means of fixing.

According to the particularly preferred exemplary embodiments illustrated in FIGS. 4 and 7, the first section extending substantially according to a first axis of extension (XX') and the second section extending substantially according to a second axis of extension (YY'), the implant 1 is bent such that the second axis of extension (YY') diverges from the first axis of extension (XX').

In a particularly preferred manner, the angle of deviation T of the second axis of extension (YY') relative to the first axis of extension (XX') is substantially between 10° and 20° inclusive, and more preferably equal to 15°. This arrangement can actually reproduce ideally the natural angling of the proximal phalange relative to the distal phalange and, more precisely, the angle formed by the medullary axes of the phalanges.

More generally, it is foreseeable to produce indifferently implants which are straight or curved so as to customize on a case-by-case basis the geometry of the implant 1 to the anatomy of the patient and/or the zone treated.

Furthermore, according to one feature which may constitute a separate embodiment, independently of the preliminary splaying during construction or of the shape of the anchoring branches, the distribution of the anchoring branches 10 associated with the first section 4, considered in a section normal to the first axis of extension (XX'), can be offset at an angle by an angle δ relative to the distribution of the anchoring branches 110 associated with the second section 6, considered in a section normal to the second axis of extension (YY').

More precisely, as is depicted in FIGS. 6-8, the first means 5 of fixing can comprise a first network of anchoring branches 10, whereas the second means 7 of fixing comprises a second network of anchoring branches 110 which incorporates the same number of branches as the first network (four in this case) arranged according to a geometry substantially similar to that of the first network, the first and second networks of branches having between them an angular offset δ, or "phase shift", substantially equal to 45°.

Indeed, the cross-sections 2T, 3T (represented by dotted lines in FIG. 8) of two successive phalanges generally have one or more favoured directions of extension and not a constant radius under all azimuths, i.e., the cross-sections 2T, 3T are not generally circular but rather ovoid or polylobed. The implant can advantageously reproduce the existing natural offset in alignment between the favoured directions of extension unique to each cross-section and thus share in each phalange the zones most provided with bony matter in order to improve the fixing, both in extent, thus in stability, and in strength.

Of course, the value of the phase shift will advantageously be chosen dependent on the bones 2, 3 involved in the operation and more precisely depending on the layout of their respective bleeding cross-sections.

Preferably, the implant 1 of the present disclosure is monobloc. Thus, the first section 4 and the second section 6 are more preferably made from the same material and fuse one with the other to form a common central section 17 from which the anchoring branches 10, 110 extend on either side.

Naturally, the implant 1 is produced in one or more biocompatible materials, more preferably titanium. It is also foreseeable, without departing from the scope of the present disclosure, to produce such an implant in a biodegradable material such as polylactide, for example, in order that the implant should be assimilated by the body once the bony fusion has taken place.

Naturally, a sufficiently rigid material will be chosen, in order that the anchoring branches can fulfil the role of immobilization and support the introduction into the bone although the anchoring branches are already splayed.

According to one particularly preferred exemplary embodiment, the implant 1 is formed by a tubular element in which the wall is split so that the ends are divided into a plurality of tongues forming the anchoring branches 10, 110.

It is foreseeable that the tubular element is formed by any sectional profile, optionally open (U-, T-, L-shaped, square, circular, and the like).

More preferably, the ends are split longitudinally and flared, i.e., the tongues are splayed radially in the space so as to be open to the outside relative to the initial section of the tubular element, and, more particularly, to form substantially a pair of cones opposite the apex, as illustrated in FIGS. 1-4, 6 and 7. Thus, the trunk 17 is more preferably longilineal and of width less than the overall diameters D1, D2 of networks of anchoring branches 10, 100 which the trunk 17 separates.

The use of a basic tubular element allows, in particular, simple and less costly manufacture of the implant 1. It also confers on the implant 1 lightness while at the same time maintaining good rigidity in flexing and good mechanical resistance to torsion.

In addition, as depicted in FIGS. 6-7, the implant 1 more preferably comprises a means of prehension 18 provided with a foolproof means arranged to inform the user of the orientation of the implant 1 at the time of attachment and handling of the implant.

Indeed, the existence of a bending and/or geometric differences between the first means 5 of fixing and the second means 7 of fixing requires precise positioning of the implant 1 relative to the first and second bones, according to a particular orientation.

The means of prehension 18 could particularly be produced with a boring made in the central trunk 17 of the implant located between the two sections 4, 6, such that a tool of conjugate form incorporating a tenon intended to cooperate in a unique and reproducible manner with the boring allows the surgeon to guarantee the directional (direction of introduction) and angular (anatomical position) orientation of the implant at the time of fitting the implant.

The present disclosure can also relate to a surgical instrument 20 for bony preparation. The instrument 20 is specifically intended for preparing a bone 2 in order to house in the bone an implant 1 having at least a first section 4 designed to be introduced into the bone and provided with a first means 5 of fixing arranged to hold the implant in the bone.

By reference to the preceding description, an instrument of the present disclosure can be employed indifferently for preparing the first and/or second bone.

According to the present disclosure, the first means 5 of fixing incorporating a plurality of anchoring branches 10 integral with the first section 4 and arranged according to a non-coplanar layout in order to create a built-in link between the implant 1 and the bones 2, 3, the instrument 20 comprises a punch 21 having a plurality of prominent elements 22 arranged so as to mark simultaneously in the bones 2, 3, by percussion, an imprint comprising a plurality of cavities 23 intended to accommodate the anchoring branches 10, the arrangement of the cavities 23 being substantially conjugate with that of the anchoring branches 10.

Of course, the instrument 20 is limited neither to a particular production shape nor to particular production dimensions and could easily be adapted depending on the various exemplary embodiments of the implant 1 described previously.

However, as the first means 5 of fixing of the implant 1 more preferably incorporates four substantially equidistant anchoring branches 10, the punch 21 will have a cruciform geometry, as is illustrated in FIG. 5A, intended to split the bone 2 according to four substantially distinct contiguous cavities 23.

As is depicted in FIG. 5B, the cavities 23 can form the lobes of a single housing 15, each of these lobes being intended to accommodate an anchoring branch 10. Naturally, the number, layout and dimensions of the cavities 23 can be adapted depending on the arrangement of the anchoring branches 10 and, in particular, form a star.

It can be noted that recourse to a housing 15 incorporating a plurality of cavities 23 separated from one another by partition elements 24 can advantageously reinforce the blocking in rotation of the first section 4 relative to the first bone 2 according to the first axis of extension (XX').

Of course, the present disclosure can also relate as such to a surgical kit comprising:

first an implant 1 of the present disclosure, and more particularly intended to be interposed between a first bone 2 and a second bone 3 in order to support the first and second bones, substantially joined one to the other, in order to obtain bony fusion of the bones, the implant 1 having at least a first section 4 designed to be introduced into the first bone and provided with a first means 5 of fixing arranged to hold the implant 1 in the first bone 2, as well as a second section 6 designed to be introduced into the second bone 3 and provided with a second means of fixing 6 arranged to hold the implant 1 in the second bone 3, the first means 5 of fixing incorporating a plurality of anchoring branches 10 integral with the first section 4 and arranged according to a non-coplanar layout so as to be able to create a built-in link between the implant 1 and the first bone 2, and second a surgical instrument 20 intended for bony preparation, the instrument comprising a punch 21 which has a plurality of prominent elements 22 arranged so as to mark simultaneously in the bone, by percussion, an imprint comprising a plurality of cavities 23 intended to accommodate the anchoring branches 10, the arrangement of the cavities 23 being substantially conjugate to that of the anchoring branches 10.

The use of an implant of the present disclosure to produce an inter-phalangeal arthrodesis will now be described in detail, by reference preferably to a surgical kit of the present disclosure.

The practitioner begins by carrying out the preparation of the first and second bones 2, 3, by resecting the ends of the bones so as to form bleeding contact surfaces of regular geometry, more preferably substantially plane.

More precisely, the practitioner excises the base of the distal phalange (the first bone 2 in FIG. 2) as well as the head of the proximal phalange (the second bone in FIG. 2).

The practitioner then fits into each end thus exposed a housing intended to accommodate the implant 1.

In order to do this, the practitioner can, for example, place against the bleeding surface an instrument 20 formed by a rod incorporating at one of the ends a cruciform punch 21 and at the other end an incus, then introduce by force the prominent elements 22 into the first bone 2 by hitting the incus on one or more occasions with an appropriate hammer.

The production of the housing 15 can also incorporate a drilling step during which the bone can be bored substantially according to its medullary axis.

Of course, according to the type of bony tissue encountered and the configuration of the joint to be treated, it is foreseeable either to punch the bone directly, or to bore a simple circular housing 15 with the drill, or first to drill a substantially cylindrical hole and then, and only then, to mark in the base and/or in the walls of the hole the cavities 23 with the cruciform punch 21.

The practitioner then grips the implant 1 with a suitable prehension instrument of the tongs type, at the same time taking care to position the implant 1 appropriately relative to the tongs with the means of prehension 18. More precisely, the tongs can incorporate a channel into which a tenon protrudes, the implant then being positioned by placing the tubular central trunk 17 in the channel so that the tenon engages in the foolproof hole fitted in the trunk.

Once the implant 1 is held in the tongs, the implant is introduced by force into the housing 15. To do this, the practitioner presses the free ends 14 of the anchoring branches 10 against the internal wall 151, into the housing channel cervix, then made to penetrate gradually by compression and/or by percussion the first section 4 inside the housing 15.

More specifically, in the case of an implant 1 comprising four equidistant anchoring branches 10 as depicted in FIGS. 1, 3, 4, 6 and 7, the practitioner has just positioned each of the anchoring branches 10 relative to one of the cavities 23 of the cruciform imprint.

Advantageously, the implant 1 is introduced in the presplayed form made during construction, the anchoring branches 10 already separated from each other, whereas the first axis of extension (XX') is presenting in a substantially parallel, or even coaxial, manner with the medullary axis of the first bone 2.

More preferably, the diameter of the housing 15 is substantially less than the overall diameter D1 of splaying at rest of the anchoring branches 10 in such a manner as, during the introduction of the first section 4 into the housing 15, the convergent portion 10B of the branches just comes into contact with the internal wall 151 in the manner of a ramp and makes the branches 10 flex gradually while turning the branches 10 down toward the first axis of extension (XX'), i.e., reduces the angle of opening $\alpha$, at least until the first section is embedded to the height of the bends 12.

Once the bends 12 have crossed the cervix of the housing 15, the bends 12 continue to slide with friction along the internal wall 151 of the housing, with the first section 4 embedded in the internal wall of the housing.

By thus constraining the branches to contract in order that the bends are positioned on a diameter substantially less than that which the bends occupy by default, an elastic stress of distortion appears between the first means 5 of fixing and the housing 15, which contributes to providing a concentric locking of the first section 4 and, consequently, of the implant 1 in the housing 15.

Moreover, the anti-return devices 16 cooperate with the internal wall 151 by penetrating into the peripheral bony tissue of the housing 15 with the movement of the first section into the housing 15, thus ensuring at any moment a stable hold of the implant by clicking.

The practitioner ceases to embed the first section 4 in the first bone 2 when the free ends 14 of the anchoring branches 10 reach the bottom of the housing 15 and/or when the junction plane between the first section 4 and the second section 6 is substantially flush with the bleeding surface of the bone.

It can be noted that the production of a housing 15 can prove optional, the anchoring branches 10 and/or the first section 4 in its entirety being then embedded directly in the material of the first bone 2, slightly in the manner of nails, starting with the bleeding surface. The free ends 14 can, for this purpose, be bevelled so as to facilitate penetration into the tissues.

Once the first section 4 is firmly anchored in the first bone 2, the practitioner can introduce the second section 6 into the second bone 3 in a similar manner.

In particular, the preparation of the second bone 3 can be substantially similar to that of the first bone 2.

Of course, the method of implanting the implant 1 of the present disclosure can be done in various ways, in particular, the order in which the first and second sections are introduced into the first and second bones respectively. As a variant, it is even foreseeable to introduce the first and second sections simultaneously into the first and second bones respectively by positioning the anchoring branches 10, 110 for each section in contact with the edge of the housings 15, 115 fitted in the corresponding bones 2, 3, then by mating the first bone 2 with the second bone 3 so as to cause the sections to penetrate simultaneously into the housings.

It may be noted that once the first and second sections are introduced into their respective bones, the first and second bones are immediately and automatically bonded with each other by the implant 1, without it being necessary to modify the conformation. The implant 1 advantageously produces a stable and rigid junction, which, in particular, eliminates any possibility of spontaneous separation or of relative movement of the bones, particularly in rotation about their respective medullary axes and in flexing at the former articulating interface.

Furthermore, the implant 1 of the present disclosure can advantageously produce a strictly internal medullary installation, as is illustrated in FIG. 2, the implant being enclosed totally in the bony mass, and, more precisely, each of the sections being inserted in their entirety into the diaphysis and/or apophysis of the corresponding bone. Advantageously, no part of the implant 1 is apparent once the first and second bones are joined, neither a fortiori flush or protruding relative to the cortical tissues of the bones. This results in a convenient and sure use of the implant, not traumatizing for the surrounding tissues.

Furthermore, the implant 1 of the present disclosure and the associated method of installation minimize the preparatory work on the bone to be set, in particular, by making one and/or the other bone completely superfluous, and/or complex machining in the fragile parts of the bones.

Finally, the present disclosure relates to a method for manufacturing a medical implant provided with a means 5, 7 of fixing, arranged to hold the implant 1 in a bone 2, 3.

According to the present disclosure, this method of manufacture comprises a step (a) for producing the means 5, 7 of fixing, during which an oblong part is scored in order to divide a fraction of the latter into a plurality of non-coplanar anchoring branches 10, 110 integral with the oblong part.

Although it can be formed by an ingot or other massive part, step (a) then implying a marking in the mass, the oblong part is more preferably formed by a hollow element, such as a profile, and, in a particularly preferred manner, by a tube of circular cross-section.

The step (a) for producing the means of fixing then includes a cutting sub-step (a1) during which one or more cuts are made from one of the ends of the hollow element and crossing the wall of the latter, in order to divide the end of the hollow element into a plurality of tongues.

In a particularly preferred manner, the cuts thus made in order to split the oblong part longitudinally according to the principal axis of extension.

The cut can advantageously be made with a laser, this method guaranteeing great accuracy for the production of implants 1 of small dimensions.

In addition, according to one important feature of the present disclosure, the step (a) for producing the means of fixing includes a splaying sub-step (a2) during which the tongues are folded outward so as to form, with the tongues, anchoring branches 10, 110 which diverge according to a substantially tapered distribution.

In other words, during the splaying sub-step (a2) of the divergent portion 10A, the anchoring branches 10 are folded outward so as to make them diverge according to a substantially tapered distribution.

In an imaged manner, the method of manufacture of the present disclosure consists more preferably substantially of "peeling" the walls of the hollow element, of deforming the walls of the hollow element plastically to burst one and/or the other of the ends of the hollow element into a corolla.

The step (a) can also incorporate a folding sub-step (a3) during which bends 12, 112 are formed by turning down the free ends of the tongues towards the axis of extension of the oblong part.

The sub-step (a3) is a sub-step forming the convergent portion 10B during which the free ends of the anchoring branches are turned down by folding towards the axis of extension of the oblong part.

Advantageously, it is possible to produce, before the folding sub-step (a3), cutting lines in a V shape at the level where the bends 12, 112 must be formed, in a manner such that the folding effected to mark the bends makes the anti-return devices 16, 116 protrude spontaneously, in this case at the apex of the bends, at the fold.

Each anti-return device is thus formed during the same operation as the corresponding bend.

It can be noted that resorting to a hollow element can advantageously limit the mass of material used, reduce the energy needed for machining, to make the element light without compromising resistance to mechanical stresses and finally to keep the cost of the implant down. The tube of circular cross-section is itself a crude format, preferred if it is a format common to numerous bio-compatible materials and widely available on the market in various sizes.

The step (a) and more precisely the sub-steps (a1) and (a2) described above can naturally be repeated, sequentially or simultaneously, at each of the ends of the oblong part so as to fashion an implant 1 as in the exemplary embodiments illustrated in FIGS. 1, 3, 4, 6 and 7.

However, the method of manufacture of the present disclosure is in no way limited to this type of implant and can, in particular, be used to produce implants having a single fixing section (or a single side), as with staples or other pins intended to support by pinching or compression any tissue (bone, muscle, tendon, and the like) against a bone and having, opposite the fixing section, a side with atraumatic contours. Such implants can, in particular, be fixed in the cortical zone of a bone, for example, by being mated against the outer surface of the bone according to a radial approach.

The method can also incorporate a bending step (b) during which the oblong part is distorted plastically in order to confer on the implant 1 an ergonomic shape which substantially reproduces the natural anatomical configuration of the zone for installing the implant. The bending step (b) can occur before or after the step (a) for producing the means of fixing.

By way of a non-limitative example, in the case of producing an inter-phalangeal implant 1 intended for foot surgery, the method of manufacture, and more precisely the sub-steps (a1) of cutting, (a2) of splaying and (a3) of folding, can be applied to a titanium tube of internal diameter equal to 2.2 mm and of wall thickness 0.5 mm, so as to produce an implant with an overall length of the order of 15 to 30 mm, more preferably 17 mm to 25 mm, and of overall diameter between 2.7 mm and 4.5 mm inclusive.

Accordingly, the implant 1 of the present disclosure has an excellent seating in the bones, which is due not only to the multiplicity of anchoring points but also to the geometry of its means of fixing, which confer on the built-in links thus produced a firm and rigid resistance, whatever the direction of the mechanical stress on the link.

Moreover, such an implant can produce the fixing of a first bone to a second bone while minimizing the magnitude and the duration of the surgical intervention, in particular, the bone preparation.

In particular, the geometry of the implant 1 facilitates its introduction and its movement into the bone, at the same time ensuring an immediate and "automatic" mechanical bond of the implant in the bone upon introduction, without requiring later manipulation.

Furthermore, the simplicity of production of such an implant advantageously allows the implant to be produced at a particularly competitive cost.

Finally, such an implant, capable of being matched in its geometry and in its dimensions for varied uses in different configurations of fixing zones, in particular, joints, guarantees excellent comfort in use for the patient because of the versatility and ergonomics of the implant.

All patents, patent applications and publications referred to herein are incorporated by reference in their entirety.

What is claimed is:

1. A medical implant interposable between a first bone and a second bone in order to support the first and second bones substantially joined one to the other, so as to obtain bony fusion of the first and second bones, the implant comprising:
    middle section having a first side and a second side;
    at least one first section having a first axis of extension extending from the first side of the middle section designed to be introduced into the first bone having a first means of fixing arranged to hold the implant in the first bone, the first means of fixing comprising a plurality of non-coplanar anchoring branches integral with the first section which are intended to create a built-in link between the implant and the first bone, each anchoring branch further having a divergent portion opened outward relative to the central axis and away from the middle section, each anchoring branch further having a convergent portion angled toward the central axis, each anchoring branch terminating in a free end; and,
    a second section extending from the second side of the middle section and having a second axis of extension designed to be introduced into the second bone and having a second means of fixing arranged to hold the implant in the second bone;
    wherein the anchoring branches are in a splayed configuration prior to implantation of the implant in the bones.

2. The implant of claim 1, wherein the anchoring branches have at least one bend which marks the transition between the divergent portion and the convergent portion, each bend having an apex.

3. The implant of claim 2, wherein the apex of the bend is provided with an anti-return device, such as a barb, arranged so as to oppose the extraction from the first bone of the corresponding anchoring branch.

4. The implant of claim 2, wherein the convergent portion extends from the bend as far as a free end of the anchoring branch.

5. The implant of claim 1, wherein the length of the divergent portion accounts for approximately 50% to 90% of the total length of the anchoring branch.

6. The implant of claim 1, wherein the first section is extended according to a first axis of extension, the angle of opening of the divergent portion relative to the first axis of extension is substantially between 5° and 20°.

7. The implant of claim 1, wherein the first section is extended according to a first axis of extension, the angle of closing according to which the convergent portion is oriented relative to the first axis of extension is substantially between 0° and 30°.

8. The implant of claim 1, wherein the anchoring branches are distributed as a corolla about the first section.

9. The implant of claim 1, wherein the first section is located at one end of the implant and the anchoring branches extend from the first section and substantially beyond the end.

10. The implant of claim 1, wherein the anchoring branches are made from the same material as the first section.

11. The implant of claim 1, wherein the first means of fixing incorporate at least three anchoring branches.

12. The implant of claim 1, wherein, the second means of fixing incorporates a plurality of anchoring branches integral with the second section and arranged according to a non-coplanar layout so as to create a built-in link between the implant and the second bone and wherein the anchoring branches are splayed during manufacture so as to have a divergent portion which opens outward relative to the first section as well as a convergent portion turning down the ends substantially in order to facilitate the introduction of the implant in the second bone.

13. The implant of claim 12, wherein the conformation of the second means of fixing is identical to that of the first means of fixing.

14. The implant of claim 1, wherein the implant is monobloc.

15. The implant of claim 1, wherein the implant is formed by a tubular element in which the wall is split at its ends such that the ends of the tube are divided into a plurality of tongues forming the anchoring branches.

16. The implant of claim 1, further comprising a means of prehension provided with a means of foolproofing arranged so as to inform the user of the orientation of the implant at the time of gripping and handling the implant.

17. The implant of claim 1, wherein the implant is an inter-phalangeal implant.

18. A medical implant interposable between a first bone and a second bone in order to support the first and second bones substantially joined one to the other, so as to obtain bony of the first and second bones, the implant comprising:
    a middle a first side and a second side;
    at least one first section having a first axis of extension extending from the first side of the middle section designed to be introduced into the first bone having a first means of fixing arranged to hold the implant in the first bone, the first means of fixing comprising a plurality of non coplanar anchoring branches integral with the first section which are intended to create a built-in link between the implant and the first bone, each anchoring branch further having a divergent portion opened outward relative to the central axis and away from the middle section, each anchoring branch further having a convergent portion angled toward the central axis, each anchoring branch each and terminating in a free end; and,
    a second section having a second axis of extension extending from the second side of the middle section designed to be introduced into the second bone and having a second means of fixing arranged to hold the implant in the second bone, the second means comprising a plurality of anchoring branches integral with the second section and arranged according to a non-coplanar layout so as to create a built-in link between the implant and the second bone and wherein the anchoring branches are in a splayed configuration prior to implantation so as to have a divergent portion which opens outward relative to the first section as well as a convergent portion turning down the ends substantially in order to facilitate the introduction of the implant in the second bone, wherein the conformation of the second means of fixing differs from that of the first means of fixing by its dimensions.

19. The implant of claim 18, wherein the first and second sections extend substantially according to the first axis of extension and according to the second axis of extension, respectively, the distribution of the anchoring branches associated with the first section, considered in a section normal to the first axis of extension, is offset at an angle relative to the distribution of the anchoring branches associated with the second section, considered in a section normal to the second axis of extension.

20. The implant of claim 19, wherein the angular offset between the network of the first anchoring branches and the network of the second anchoring branches is substantially equal to 45°.

21. A medical implant interposable between a first bone and a second bone in order to support the first and second bones substantially joined one to the other, so as to obtain bony fusion of the first and second bones, the implant comprising:

a middle section having a first side and a second side;

at least one first section having a first axis of extension extending from the first side of the middle section designed to be introduced into the first bone having a first means of fixing arranged to hold the implant in the first bone, the first means of fixing comprising a plurality of non-coplanar anchoring branches integral with the first section which are intended to create a built-in link between the implant and the first bone, each anchoring branch further having a divergent portion opened outward relative to the central axis and away from the middle section, each anchoring branch further having a convergent portion angled toward the central axis, each anchoring branch each and terminating in a free end; and, a second section having a second axis of extension extending from the second side of the middle section designed to be introduced into the second bone and having a second means of fixing arranged to hold the implant in the second bone, the second means comprising a plurality of anchoring branches integral with the second section and arranged according to a non-coplanar layout so as to create a built-in link between the implant and the second bone and wherein the anchoring branches are in a splayed configuration prior to implantation so as to have a divergent portion which opens outward relative to the first section as well as a convergent portion turning down the ends substantially in order to facilitate the introduction of the implant in the second bone, wherein the first and second sections extend substantially according to the first axis of extension and according to the second axis of extension, respectively, and wherein the implant is bent such that the angle of deviation of the second axis of extension relative to the first axis of extension is substantially between 10° and 20°.

22. A surgical kit, comprising:

a) an implant interposable between a first bone and a second bone in order to support the first and second bones substantially joined one to the other, so as to obtain bony fusion of the first and second bones, the implant comprising at least one first section designed to be introduced into the first bone having a first means of fixing arranged to hold the implant in the first bone, as well as a second section designed to be introduced into the second bone and having a second means of fixing arranged to hold the implant in the second bone, wherein the first means of fixing incorporates a plurality of non-coplanar anchoring branches integral with the first section which are intended to create a built-in link between the implant and the first bone, wherein anchoring branches, each having a convergent portion having an end and further having a divergent portion, are splayed during manufacture of the implant so that, before installation of the implant in the bones, the divergent portion of each branch opens outward relative to the first section and the ends of the convergent portion substantially turn down in order to facilitate the introduction of the implant into the first bone; and b) a surgical instrument for bony preparation, the instrument comprising a punch having a plurality of prominent elements arranged so as to mark simultaneously in the bone, by percussion, an imprint comprising a plurality of cavities intended to accommodate the anchoring branches of the implant, the arrangement of the cavities are substantially conjugate to that of the anchoring branches.

23. A method for manufacturing a medical implant, comprising:

a) producing a first means of fixing having a central axis during which an oblong part is cut so as to divide a fraction of the oblong part into a plurality of the non-coplanar anchoring branches integral with the oblong part, each branch having a free end b) deploying the divergent portion during which the anchoring branches are folded outward so as to cause them to diverge according to a substantially tapered distribution, and c) forming a convergent portion during which the free ends of the anchoring branches are turned down by folding toward the central axis of the oblong part.

24. The method of claim 23, wherein step (a) forming the convergent portion can form a bend by folding between the divergent portion and the convergent portion so that the step (c) forming the convergent portion is preceded by making cut lines such that the marking of the bend by folding causes an anti-return device, such as a barb, to protrude at the apex of the bend.

* * * * *